(12) United States Patent
Guidotti et al.

(10) Patent No.: US 8,039,684 B2
(45) Date of Patent: Oct. 18, 2011

(54) ABSORBENT ARTICLE COMPRISING A LIQUID-PERMEABLE MATERIAL LAYER

(75) Inventors: Ted Guidotti, Göteborg (SE); Gunnar Edvardsson, Bohus Björkö (SE)

(73) Assignee: SCA Hygiene Products AB, Gothenburg (SE)

( * ) Notice: Subject to any disclaimer, the term of this patent is extended or adjusted under 35 U.S.C. 154(b) by 411 days.

(21) Appl. No.: 12/086,920

(22) PCT Filed: Dec. 21, 2005

(86) PCT No.: PCT/SE2005/002007
§ 371 (c)(1),
(2), (4) Date: Jun. 20, 2008

(87) PCT Pub. No.: WO2007/073254
PCT Pub. Date: Jun. 28, 2007

(65) Prior Publication Data
US 2009/0036854 A1  Feb. 5, 2009

(51) Int. Cl.
*A61F 13/15* (2006.01)
(52) U.S. Cl. ... 604/378; 604/379; 604/380; 604/385.12; 604/377; 604/376; 604/375; 604/374; 604/367; 604/369
(58) Field of Classification Search ............... 604/369, 604/367, 374–380, 385.12
See application file for complete search history.

(56) References Cited

U.S. PATENT DOCUMENTS

| | | | |
|---|---|---|---|
| 4,381,783 A | 5/1983 | Elias | |
| 4,676,785 A * | 6/1987 | Battista | 604/369 |
| 5,797,892 A * | 8/1998 | Glaug et al. | 604/361 |
| 5,935,118 A * | 8/1999 | Gryskiewicz et al. | 604/385.02 |
| 5,938,650 A * | 8/1999 | Baer et al. | 604/368 |
| 6,102,892 A | 8/2000 | Putzer et al. | |
| 6,159,190 A | 12/2000 | Tanaka et al. | |
| 6,162,961 A * | 12/2000 | Tanner et al. | 604/374 |
| 6,191,340 B1 | 2/2001 | Carlucci et al. | |
| 6,245,410 B1 | 6/2001 | Hähnle et al. | |
| 6,958,430 B1 | 10/2005 | Marinelli | |
| 7,767,875 B2 * | 8/2010 | Olson et al. | 604/361 |
| 7,799,967 B2 * | 9/2010 | Ranganathan et al. | 604/369 |
| 2004/0193127 A1 | 9/2004 | Hansson et al. | |
| 2004/0193129 A1 | 9/2004 | Guidotti et al. | |

(Continued)

FOREIGN PATENT DOCUMENTS

CN  1209989 A  3/1999

(Continued)

OTHER PUBLICATIONS

Chinese Office Action issued in corresponding Chinese Patent Application No. 200580052376.6, mailed Jul. 8, 2010.

(Continued)

*Primary Examiner* — Jacqueline F Stephens
(74) *Attorney, Agent, or Firm* — Buchanan Ingersoll & Rooney PC

(57) ABSTRACT

An absorbent article includes at least one liquid-permeable layer material (105) and an absorbent structure (106), the absorbent structure (106) having the ability to expand on wetting, which entails that the absorbent structure (106) displays a first volume in dry condition and a second volume in completely expanded wet condition, the second volume being greater than the first volume. The liquid-permeable layer material (105) encloses the absorbent structure (106) so that the absorbent structure (106) is prevented from reaching complete expansion during wetting.

13 Claims, 5 Drawing Sheets

U.S. PATENT DOCUMENTS

2004/0254549 A1 * 12/2004 Olson et al. .................. 604/361

FOREIGN PATENT DOCUMENTS

| CN | 1371671 A | 10/2002 |
|---|---|---|
| EP | 0 804 916 A1 | 4/1996 |
| EP | 0 804 917 A1 | 11/1997 |
| EP | 0 834 296 A1 | 4/1998 |
| RU | 2 278 649 | 6/2006 |
| WO | WO 97/40796 A1 | 11/1997 |
| WO | WO 98/00081 A1 | 1/1998 |
| WO | WO 98/22057 A1 | 5/1998 |
| WO | WO 98/22062 A1 | 5/1998 |
| WO | WO 00/02509 A1 | 1/2000 |
| WO | WO 02/41817 A1 | 5/2002 |
| WO | WO 02/47594 | 6/2002 |

OTHER PUBLICATIONS

Decision on Grant Patent for Invention issued in the corresponding Russian Application No. 2008129677, Jul. 21, 2008.
PCT/ISA/210, Nov. 7, 2006.
PCT/ISA/237, Nov. 7, 2006.
PCT/IPEA/409, Oct. 22, 2007.

* cited by examiner

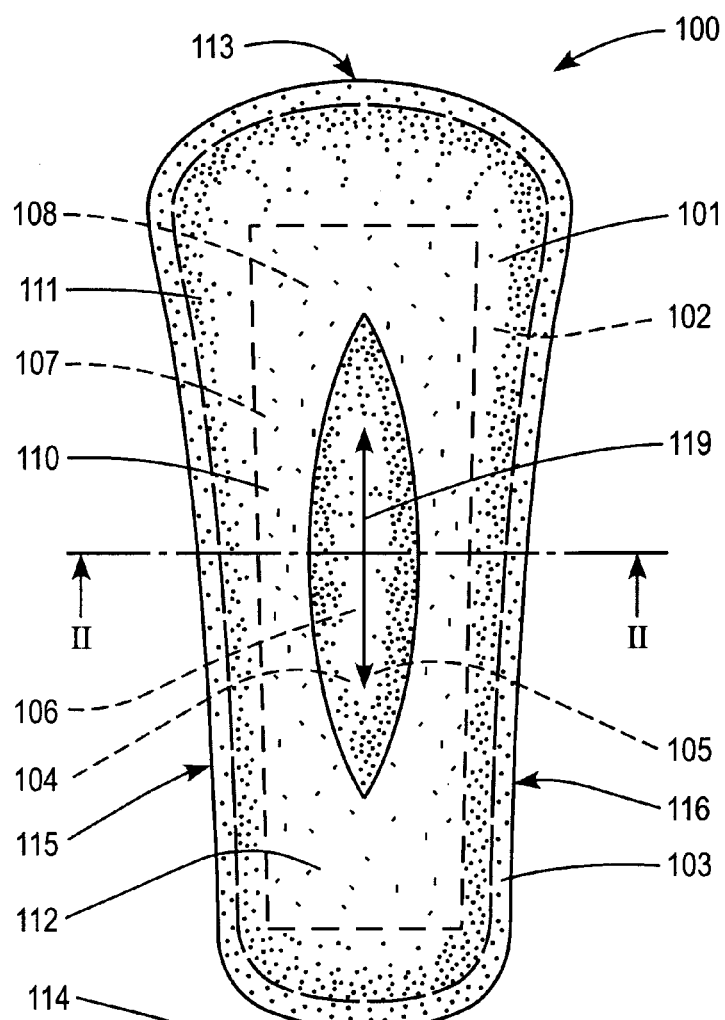
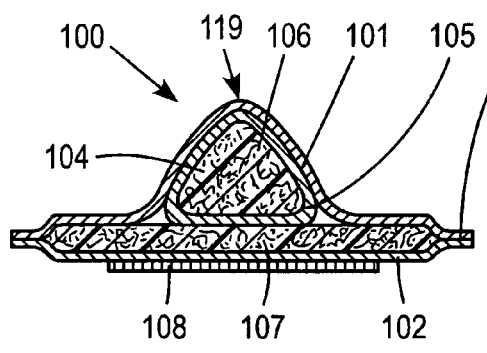 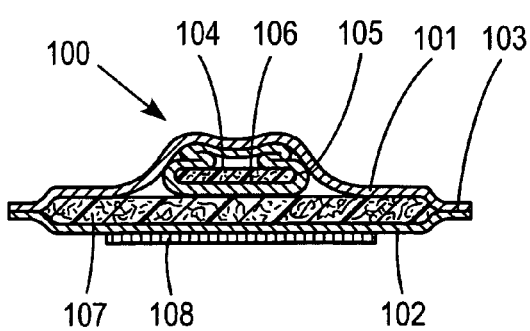
FIG. 1
FIG. 2a  FIG. 2b

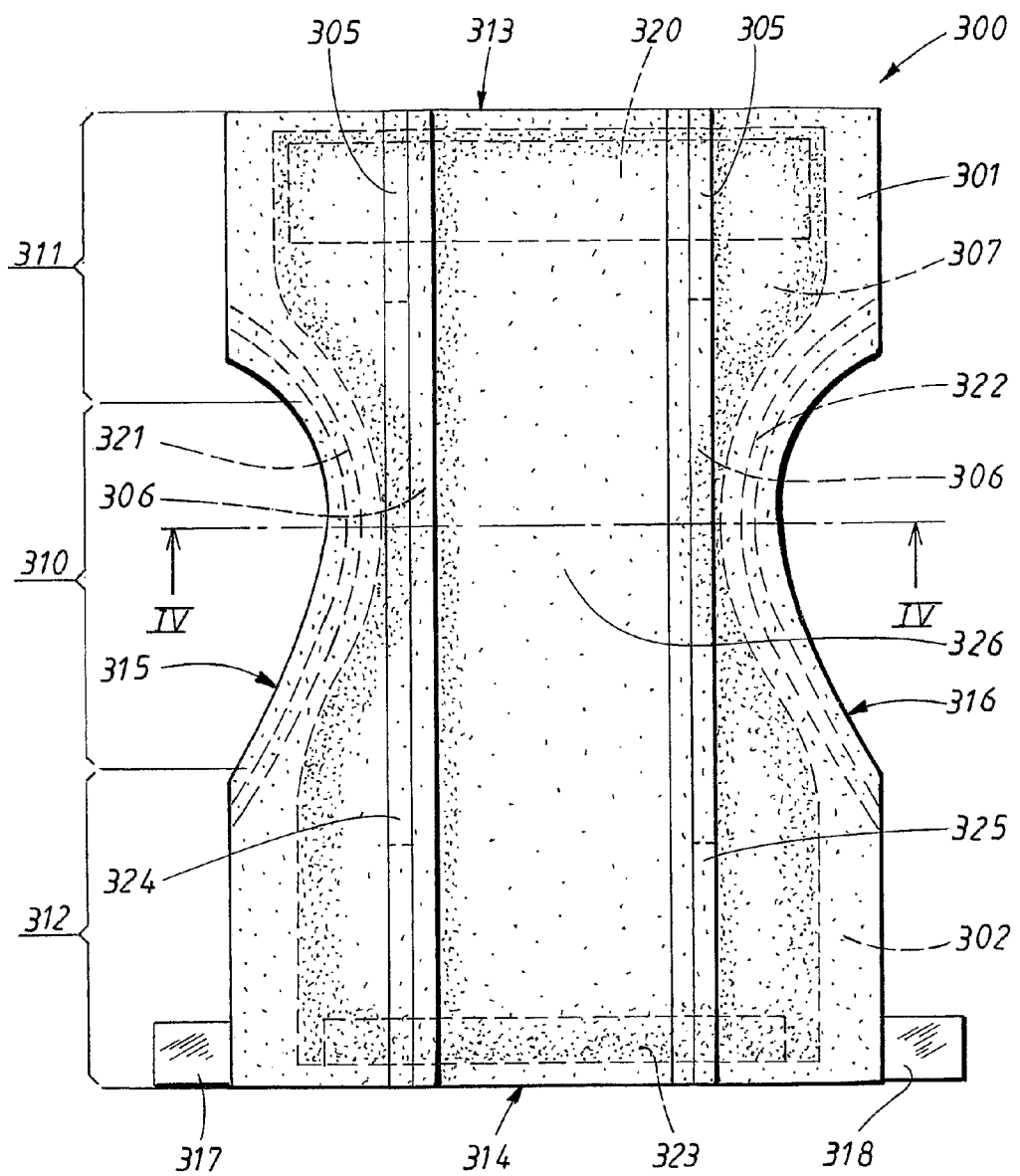
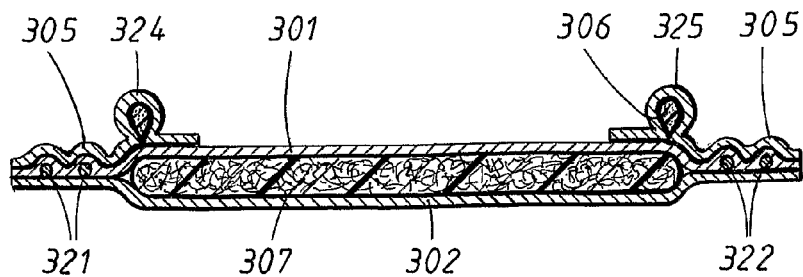

US 8,039,684 B2

ABSORBENT ARTICLE COMPRISING A LIQUID-PERMEABLE MATERIAL LAYER

TECHNICAL FIELD

The present disclosure concerns an absorbent article comprising a liquid-permeable surface layer and a liquid-impermeable surface layer and also an absorption body arranged between the surface layers, the absorption body comprising at least one liquid-permeable material layer and an absorbent structure, the absorbent structure having the ability to expand on wetting, which entails that the absorbent structure displays a first volume in dry condition and a second volume in completely expanded wet condition, the second volume being greater than the first volume.

BACKGROUND ART

Absorbent articles such as diapers, incontinence protectors and sanitary napkins are intended to receive and absorb body fluids such as urine and menstrual fluid. Of course, articles with different forms and sizes exist depending on the area of use and the amount of fluid the article must be able to absorb. For example, diapers for heavily incontinent adults are considerably larger and have greater absorption capacity than diapers for babies. Furthermore, in addition to the requirements for sufficient absorption capacity and leakage security, there is also a requirement that the diaper be comfortable to wear. For adult users it is also important that the articles are discreet and can be worn without being noticed under normal clothing. A further important criterion for absorbent articles intended for single use is that they do not take up too much space during storage, transport and in the package bought by the consumer.

In order to obtain a sanitary napkin which has a good fit, it is known to produce articles with a three-dimensionally formed, anatomically adapted form. Absorbent articles which comprise shape-stable stiff members are described in SEA-9604223-9 and SE-A-9604221-3. The shape-stabilising members, or forming members, are three-dimensionally formed members constructed from materials which resist wrinkling or flattening when they are subjected to forces from the user's body, for example when the user walks or sits on the article. Although the three-dimensional shape solves the problem of obtaining a good fit during use of the absorbent articles, three-dimensional absorbent articles entail considerable difficulties during manufacturing and storage. Three-dimensional parts are difficult to handle in a manufacturing process, for example when they have to be assembled to make an absorbent article.

EP 0 834 296 A1 concerns an absorbent article which is flat in dry condition but which expands on wetting to a predetermined, three-dimensional profile. The absorbent article has an expanded layer, preferably a foam of regenerated cellulose, i.e. viscose foam. Furthermore, the absorbent article has a liquid-permeable surface material. The liquid-permeable surface material has pleats in dry condition, which pleats unfold on wetting so that the expanding layer can swell to several times its dry volume. However, a problem with such an article is that viscose foams are very soft after being wetted. A further problem with the known article is that viscose foams have an insufficient liquid-retaining ability.

SUMMARY

The disclosure therefore aims to remedy the problems with the previously known expanding articles. A particular aim of the invention is to achieve an absorbent article with a shape-stable three-dimensional structure.

An article of the type described in the introduction has been achieved. The article enables an efficient use of the absorption capacity of a swellable absorbent article in order to give a better fit and to minimise the occurrence of leakage.

The absorbent article comprises at least one liquid-permeable layer and an absorbent structure, the absorbent structure having the ability to expand on wetting and having a first volume in dry condition and a second volume in completely expanded wet condition, the second volume being greater than the first volume. An absorbent article is chiefly characterised in that the liquid-permeable material layer constitutes volume-limiting means for the absorbent structure so that the absorbent structure is prevented from reaching complete expansion on wetting.

In this way, the stiffness of the absorbent structure increases when it is wetted, whereby the swelled absorbent structure with the volume-limiting means in wet condition forms a shape-stable forming element. An advantage of such an article is that it is flat before wetting, but that it displays a more three-dimensional form when it is wet.

The liquid-permeable material layer thus defines and limits the available expansion space for the absorbent structure. The material layer can be in the form of a continuous material layer which is arranged around the absorbent structure in such a way that complete expansion of the absorbent structure is prevented. Alternatively, the material layer can be in the form of two or more material layers which have been joined together to make a surrounding sleeve around the absorbent structure. It is also possible to arrange the absorbent structure in a space between the liquid-permeable material layer and one of the other components in the absorbent article, for example one of the cover layers of the article. It is not necessary that the expansion space is completely closed around the absorbent structure. For example, elongated absorbent structures can be enclosed in tube-shaped sleeves or other spaces with open ends or open parts. What is essential is that swelling of the absorbent structure is limited in the desired swelling direction and in the desired parts of the absorbent structure.

By adapting the size and shape of the liquid-permeable material layer in relation to the size and shape of the absorbent structure, it is possible to predetermine the swelled/expanded form of the absorbent structure and thus give the absorbent article a three-dimensional form which is adapted to the user's body, or which gives the article raised barriers or other three-dimensional functional elements.

Due to the fact that the liquid-permeable material layer limits the expansion space of the absorbent structure, the absorbent structure, after wetting, will press against the liquid-permeable material layer and keep it expanded in the desired predetermined form. The expansion force in the absorbent structure also entails that the forming element formed on wetting exerts a counterforce when the forming element is subjected to compressive forces during use, for example when the user walks or sits down. This means that a formed forming element has an extremely good ability to resist undesired compression or other deformation.

A further advantage with an article of this type is that the absorbent article is flat during the manufacturing process. As has been mentioned above, three-dimensional parts are difficult to handle in a manufacturing process, for example when they have to be put together to make an absorbent article.

In addition, it is an advantage that the absorbent article is flat before use as it is thus easier to package and occupies a smaller space in the packaging.

According to one embodiment, the absorbent structure, after wetting, forms a forming element which is shape-stable. This means that the forming element is not deformed by the compressive forces acting in the article, which forces arise during normal use of the article, i.e. when the user sits, lies, stands or moves with the article in contact with his/her body. An advantage of such an article is that the absorbent structure, after wetting, forms one or several shape-stable, stiff members, which resist wrinkling or flattening when they are subjected to forces from the user's body. The forming element can, for example, form a raised portion on the surface which is covered by the liquid-permeable surface layer or constitute an internal shape-stable element in the absorption body.

According to a further embodiment, the absorbent structure can expand when wetted to a maximum volume which is ⅔ of the second volume of the absorbent structure. In order to achieve a good effect from the expansion restriction, the absorbent structure should have an expansion capacity which is 100%-5000% and preferably 200%-4000%. Expansion capacity denotes the ability of the absorbent structure to increase in volume when taken from dry condition to wet condition without expansion limitation. The expansion capacity can be determined, for example, with the Volume Increasing Method described below.

The absorbent structure is advantageously a polyacrylate-based foam material. A polyacrylate-based superabsorbent foam material is manufactured by saturating a solution consisting of at least monomers, crosslinkers, initiators and tenside and pressurising it with carbon dioxide in a receptacle while stirring. When the solution is removed from the receptacle through a nozzle, the solution expands and a foamed structure is obtained. The foamed structure is then locked due to polymerisation and crosslinking being initiated by means of, for example, UV-radiation. Finally, the material is compressed and dried. A polyacrylate-based foam of this type is described in detail in Example 1.

Another type of absorbent structure which can be used comprises a mixture of superabsorbent material and fibres. Superabsorbent material denotes absorption material with the ability to take up and bind liquid corresponding to several times its own weight while forming a swelled hydrogel. The fibres preferably comprise absorbent fibres, such as cellulose fluff pulp, viscose fibres, cotton or the like. It is also possible to use mixtures of non-absorbent fibres and absorbent fibres, or only non-absorbent fibres. Non-absorbent fibres are, for example, various types of synthetic fibres of polymers, such as polyolefines, polyester and polyamide.

It is also possible to use pure cellulose fibre structures with high density. For example, an absorbent structure of cellulose fluff pulp with a density of at least 0.3 g/cm$^3$ can be used. The density of the cellulose fibre structure is determined on a rectangular material sample, wherein the weight, area and thickness of the material are measured and the density is calculated from the measured values. The thickness of the sample is determined at a pressure of 0.5 kPa. All measurements are carried out at 23° C. and 50% relative humidity.

The liquid-permeable material layer can consist of or comprise a nonwoven material. The liquid-permeable material layer can also consist of or comprise an apertured plastic film or a net material.

According to one embodiment, the absorbent article has two longitudinal side edges, wherein the absorbent structure, after swelling, forms raised liquid barriers arranged along the longitudinal side edges. One advantage of such an embodiment is that the absorbent structure, after the first wetting, acts as raised liquid barriers. A further advantage of such an embodiment is that the absorbent structure has the ability, even on the first wetting, to prevent fluid leakage along the longitudinal side edges due to the fact that fluid is taken up and stored by the absorbent structure.

A problem that is connected to conventional elasticated leakage barriers ("standing gathers") which are intended to form pockets for gathering liquid is that they can be compressed and flattened when they are subjected to excessive external pressure. When the elastic barriers are compressed, the pockets are more or less closed whereupon the liquid is prevented from flowing in to the pockets and instead runs over the barriers. The described problem with conventional elasticated leakage barriers is eliminated with the raised liquid barriers since the absorbent structure forms, after wetting, a permanent raised portion which is essentially shape-stable.

According to another embodiment, the absorbent article has a thickness direction, the absorbent structure having an acquisition area for receiving body fluid, consisting of at least a cavity or an area with lower density than a part of the absorbent structure that is adjacent to the acquisition area and is situated chiefly on the same plane. The part that is adjacent to the acquisition area comprises the absorbent structure, wherein the absorbent structure chiefly increases in diameter in the thickness direction of the article during wetting and the size of the acquisition area increases in this direction during wetting. In this way, a cavity, or a well, is formed, which has the ability to take up liquid during subsequent wettings.

According to a further embodiment, the absorbent structure, in dry condition, has a density that is at least 0.5 g/cm$^3$. According to a similar embodiment, the absorbent structure; in dry condition, has a density that is at least 0.7 g/cm$^3$. An advantage of an embodiment like this is that the superabsorbent foam is thin before wetting.

The dry density denotes the density that the absorbent structure has in the absorbent article during storage of the absorbent articles, for example in a sealed diaper package. Diaper package refers to the package in which the diapers are enclosed for sale. In some cases, diapers can be individually wrapped, a number of individually wrapped diapers then being sealed in a larger diaper package. Diaper package then does not refer to the individually wrapped diaper but to the larger, outer diaper package. Similarly, if the absorbent article is an incontinence protector or a sanitary napkin, the density referred to is the density that the absorbent structure has in the absorbent article during storage of the absorbent articles in the sealed incontinence protector package or the sealed sanitary napkin package. When the density of the absorbent structure is measured, the measurement should be carried out within 2 minutes from the packaging being opened. The density should be measured with a load of 0.5 kPa on the material.

According to a further embodiment, the total absorption capacity per cubic centimeter of the absorbent structure in dry condition is at least 15 g/cm$^3$. According to a more preferred embodiment, the total absorption capacity per cubic centimeter of the absorbent structure in dry condition is at least 27 g/cm$^3$. According to an even more preferred embodiment, the total absorption capacity per cubic centimeter of the absorbent structure in dry condition is at least 35 g/cm$^3$ Example 2 describes in detail how the absorption capacity in the absorbent structure is measured.

BRIEF DESCRIPTION OF THE DRAWINGS

The invention will be described below in more detail with reference to the figures shown in the attached drawings, in which FIG. 1 shows a sanitary napkin in accordance with an embodiment of the invention, FIG. 2a shows a cross section along the line II-II through the sanitary napkin in FIG. 1 after wetting, FIG. 2b shows a cross section along the line II-II through the sanitary napkin in FIG. 1 before wetting, FIG. 3 shows a diaper with liquid barriers in accordance with an embodiment of the invention FIG. 4 shows a cross section along the line IV-IV through the diaper in FIG. 3.

DETAILED DESCRIPTION OF THE PREFERRED EMBODIMENTS

Figure 5:
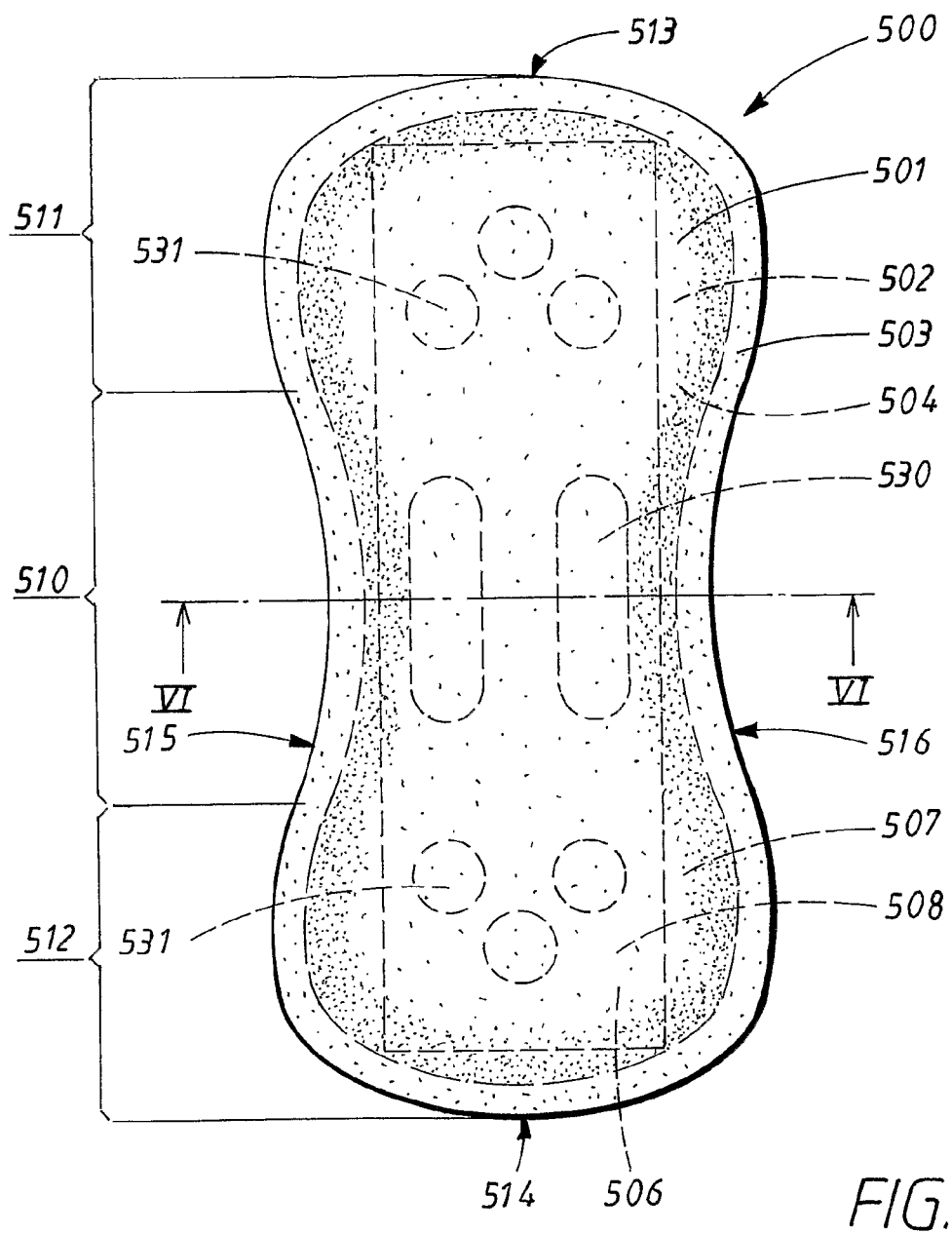
FIG. 5 shows an incontinence protector with a forming element consisting of an absorbent structure in accordance with an embodiment of the invention.

The sanitary napkin 100 shown in FIG. 1 comprises a liquid-permeable cover layer 101 arranged on the side of the sanitary napkin that is intended to be facing towards the user during use. Examples of liquid-permeable cover layers 101 that can be used are various types of nonwoven material, perforated plastic films, nets, or laminates of these.

The sanitary napkin 100 further comprises a backing layer 102 arranged on the side of the sanitary napkin that is intended to be facing away from the user during use. The backing layer 102 is suitably essentially liquid-impermeable or completely liquid-impermeable.

The liquid-permeable cover layer 101 and the backing layer 102 are mutually joined and form a projecting joining edge 103 around the periphery of the sanitary napkin. The join between the layers can be achieved with any known technique suitable for the purpose, such as gluing or welding with heat or ultrasound.

Between the liquid-permeable cover layer 101 and the backing layer 102 in a direction from the liquid-permeable cover layer 101 towards the backing layer 102, there is a forming element 104, which is shown in swelled and unswelled condition (FIGS. 2a and 2b, respectively), and an absorption body 107.

The sanitary napkin 100 has an elongated form with a front transverse end edge 113, a rear transverse end edge 114 and two longitudinal side edges 115, 116. The sanitary napkin 100 can also be divided into three portions with regard to how the sanitary napkin is to be worn in relation to a user's body. Thus, the sanitary napkin has a front end portion 111, a rear end portion 112 and a crotch portion 110 situated between the end portions 111,112.

A fastening member 108 in the form of a longitudinal rectangular area of self-adhesive glue is arranged on the surface of the backing layer 102 that faces away from the user. The fastening member 108 extends over most of the surface of the backing layer 102 between the two end edges 113, 114. Before use, the fastening member 108 is suitably covered by a releasable protective layer, for example of siliconised paper.

It is possible, of course, to use other glue patterns than that shown, such as for example longitudinal stripes, transverse areas, dots or other figures. In addition, the type of fastening member has of course no significance for the invention, it being possible to use friction fastening and various types of mechanical fastening devices, such as wings or the like, alone or in combination with one another. It is also possible to dispense altogether with the use of fastening devices.

The extension and location of the forming element 104 correspond on the whole with the form and size of the crotch portion 110 of the sanitary napkin 100. The forming element 104 is constituted by a liquid-permeable material layer 105 and an absorbent structure 106, the absorbent structure 106 having the ability to expand when wetted, with the result that the absorbent structure 106 has a first volume in dry condition and a second volume in completely expanded wet condition, the second volume being greater than the first volume. The liquid-permeable cover layer 105 surrounds the absorbent structure 106 so that the absorbent structure 106, when wetted, is prevented from reaching complete expansion. It is essential that the liquid-permeable cover layer 105 is arranged around the absorbent structure 106 in such a way that the expansion space is limited by the material layer 105. This can be achieved, for example, by the material layer 105 being in the form of a seamless tube, or having been made into a tube by joining two edges of an initially flat material layer. It is also possible to achieve a limited expansion space by attaching the material layer 105 to another component, for example, the absorption body 107.

Due to the fact that the expansion space is limited, the absorbent structure 106, after wetting, forms a raised portion which is essentially shape-stable, whereby the sanitary napkin 100 is not deformed by the pressure forces acting in the napkin 100, which occur during normal use of the napkin 100. The forming element 104, after wetting, has a predetermined three-dimensional form with a central raised portion 119 extending in the longitudinal direction of the sanitary napkin. During use of the sanitary napkin 100, the central raised portion 119 shall be in contact with the user's body and shall be partly inserted between the user's outer labia.

The central raised portion 119 has a longitudinal shape and becomes narrower towards the end portions 111, 112 of the sanitary napkin 100. The raised portion is highest at the area which is intended to be arranged at the user's vaginal opening during use.

The absorption body 107 is arranged between the forming element 104 and the backing layer 102. The absorption body 107 is suitably constituted by one or several layers of some conventional absorption material. Examples of materials which can be used are tissue layers, wadding layers of synthetic or natural fibres, layers of cellulose fluff pulp, absorbent foam layers or the like.

Examples of materials for the absorbent structure are polyacrylate-based foam materials.

FIG. 2a shows in cross section how the forming element 104 appears when the absorbent structure 106 is wet and has swollen so that it fills the available expansion space inside the liquid-permeable material layer 105. Due to the fact that the absorbent structure 106 cannot expand freely but is limited by the liquid-permeable material layer 105, this layer is held stretched out so as to form a shape-stable, stiff raised portion 119 with low compressibility at the surface of the sanitary napkin 100 that is intended to be in contact with the user's body during use. The shape of the raised portion 119 is determined by the shape of the available space which is defined by the liquid-permeable cover layer 105.

FIG. 2b shows an example of how the forming element 104 and the liquid-permeable cover layer 105 can be arranged before wetting. The liquid-permeable cover layer 105 has a folded part 109 which can open out when the absorbent structure 106 swells. An alternative or complementary way to obtain expansion space is by forming the liquid-permeable cover layer 105 from an extensible material with limited and predetermined extensibility. In both cases the expansion space must be adapted so that the absorbent structure cannot expand completely.

The diaper 300 shown in FIGS. 3 and 4 has a conventional basic construction and comprises a liquid-permeable cover layer 301, a liquid-impermeable backing layer 302 and an absorbent body 307 arranged between the liquid-permeable cover layer 301 and the liquid-impermeable backing layer 302. The liquid-permeable cover layer 301 is suitably a soft, skin-friendly and pliable material of nonwoven, perforated plastic film, net, or the like. It is common to use polymer materials which are in themselves hydrophobic but which have been treated to obtain a hydrophilic surface so that liquid can pass through the layer. A hydrophilised surface material of this type is advantageous because it does not absorb liquid and thus retains a dry surface. Various types of laminates and combinations of different nonwoven layers and/or plastic film layers can also be used. A thin plastic film is usually used as the liquid-impermeable backing layer 302 but it is also possible to use laminates and combinations of plastic films and nonwoven, hydrophobic nonwoven materials, or the like. It is an advantage if the backing layer has a certain breathability so that air and water vapour can pass through the layer.

The absorption body is also of conventional type and can thus consist of one or several layers of absorbent material, for example cellulose fluff pulp with or without the addition of superabsorbents. The absorption body can also comprise liquid-acquisition layers, liquid-distribution layers, stabilising members, binding agents, etc.

The diaper 300 has an hour-glass form with a longitudinal direction and a transverse direction and can be divided in the longitudinal direction into a broader front portion 311 and rear portion 312 and also an intermediate narrower crotch portion 310. In addition, the diaper has a front transverse end edge or waist edge 313, a rear transverse end edge or waist edge 314, and two longitudinal side edges 315, 316.

To enable the diaper to be fastened together into a pant shape around the lower part of the user's torso, the diaper is provided with two fastening tabs 317, 318 arranged projecting from either side edge 315, 316, parallel with the rear waist edge 314.

When the diaper 300 is put on, it is arranged with the front portion 311 over the user's stomach, the rear portion 312 over the user's buttocks and the crotch portion between the user's legs. The diaper 300 is then fastened together around the user's waist by the fastening tabs 317, 318 being taken over the front portion 311 and fastened on a reception area 320 on the outside of the front portion 311. The fastening tabs can be adhesive tape tabs, or comprise one part of a hook-and-loop fastening arrangement. It is most common that the fastening tabs are provided with the hook members of the hook-and-loop fastening arrangement and that the reception area has the corresponding loop members. These can be in the form of a nonwoven material with fibre loops into which the hook members can hook. If the outer surface of the diaper consists of such a nonwoven material, no particular reception area is required. In the same way, a particular reception area for adhesive fastening tabs can be dispensed with if the outer surface is a plastic film which in itself has sufficient strength to bear fastening and preferably also opening and reclosing of the tape tabs.

The shown fastening member in the form of fastening tabs 317, 318 is of course not necessary for the invention, it being possible to use other suitable fastening members such as belts, buttons, hook-and-eye, or the like.

In order to give a good fit and to increase leakage security, the diaper 300 is provided with leg elastic 321, 322 in the form of elastic threads or bands which are arranged pre-stretched along those parts of the side edges 315, 316 which form leg openings when the diaper 300 is worn. In a corresponding manner, an elastic band or the like is arranged along the rear waist edge 314 and forms waist elastic 323. The diaper 300 is shown in the figures with the elastic members 321, 322, 323 in stretched condition. When the stretching ceases, the elastic is drawn together and gives the diaper a three-dimensional form with wrinkled edges.

The diaper also has two longitudinal liquid barriers 324, 325 arranged in the longitudinal direction on either side of a central liquid acquisition area 326 on the diaper. The liquid barriers each comprise a liquid-permeable material layer 305 which has been formed into a tunnel around an absorbent structure 306, as can be best seen in FIG. 4. In the shown example, the barrier tunnels are formed in separate material strips which are fastened, for example, with glue or ultrasound welding on the surface 301 of the liquid-permeable cover layer. Alternatively, it is possible to form the barrier tunnels in the liquid-permeable cover layer 301 and to exclude the specific material strips.

The liquid barriers 324, 325 are constituted by a liquid-permeable material layer 305 and an absorbent structure 306, the absorbent structure 306 having the ability to expand when wetted, with the result that the absorbent structure 306 has a first volume in dry condition and a second volume in completely expanded wet condition, the second volume being greater than the first volume. The liquid-permeable cover layer 305 surrounds the absorbent structure 306 so that the absorbent structure 306, when wetted, is prevented from reaching complete expansion. It is essential that the liquid-permeable cover layer 305 is arranged around the absorbent structure 306 in such a way that the expansion space is limited by the material layer 305. This can be achieved, for example, by the material layer 305 being in the form of a seamless tube, or having been made into a tube by joining two edges of an initially flat material layer. It is also possible to achieve a limited expansion space by attaching the material layer 305 to another component.

Due to the fact that the expansion space is limited, the absorbent structure 306, after wetting, forms a portion which is essentially shape-stable, whereby the absorbent structure 306 is not deformed by the pressure forces acting on the diaper 300, which occur during normal use. The liquid barriers 324, 325, after wetting, have a predetermined three-dimensional form extending in the longitudinal direction of the sanitary napkin.

In the shown example, the absorbent structure 306 extends only within that part of the diaper 300 which is situated around the leg openings when the diaper is being worn. Consequently, the absorbent structure 306 is in the crotch portion 310 and extends a short distance into the front portion 311 and the rear portion 312, respectively. The shown embodiment gives good leakage security with raised barriers around the leg edges but leaves the front and rear portions 311, 312 of the diaper smooth and in contact with the user's body during use.

Naturally, it is possible to arrange expanded barriers over a greater or smaller part of the length of the diaper than that shown. It is also possible to arrange swellable barriers at the waist edges of the diaper or as liquid control members anywhere on the liquid-permeable surface of the diaper where it is desirable to direct the liquid flow. For example, it is possible to create channels in order to lead the liquid towards the end portions of the diaper by arranging parallel expandable barriers at the wetting area of the diaper, i.e. the part of the diaper that is intended to be wetted first by body fluids. When the user excretes liquid to the wetting area, the barriers swell up and form liquid transport channels between them.

Figure 6:
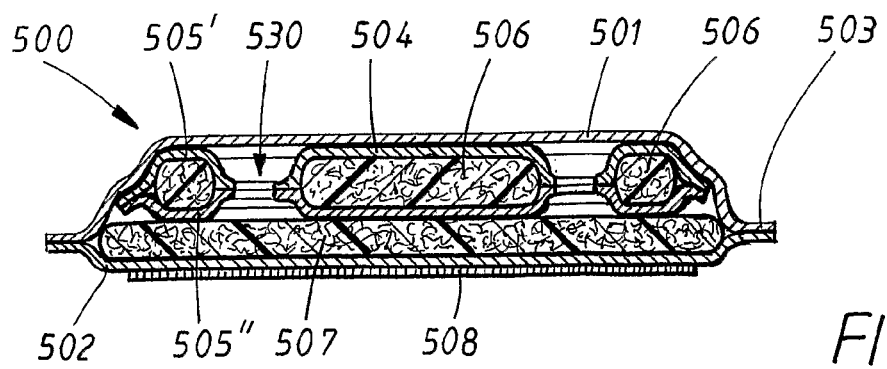
FIG. 6 shows a cross section along the line VI-VI through the incontinence protector in FIG. 5.

FIGS. 5 and 6 show an incontinence protector 500 comprising a liquid-permeable cover layer 501 and a liquid-impermeable backing layer 502, which are mutually attached in a joining edge 503 and together enclose an absorption body 507 and a forming element 504. The forming element 504 consists of a layer of an absorbent structure 506 which is enclosed between two liquid-permeable material layers 505', 505" which have been joined together, for example, by gluing or welding. The forming element 504 is placed on the absorption body 507 between the absorption body and the liquid-permeable cover layer 501 and serves as a liquid transfer member to the absorption body 507. The absorption body 507 suitably consists of an absorbent material with high absorption capacity and retention ability, for example a mixture of cellulose fluff pulp and superabsorbents. Due to the absorbent structure 506 itself having a good absorption ability, the absorption capacity obtained by the forming element 504 can be sufficient for certain applications, for example for incontinence protectors intended to be used for light incontinence. In such an embodiment, the absorption body 507 can be excluded, or formed as a thin security layer with low absorption capacity, for example a tissue material.

The incontinence protector 500 has an hour-glass shape with two end portions 511, 512 and an intermediate crotch portion 510, as well as transverse end edges 513, 514 and longitudinal side edges 515, 516.

Like the sanitary napkin 100 shown in FIGS. 1 and 2, the incontinence protector 500 is provided with an adhesive fastening member 508 on the outside of the liquid-impermeable backing layer 502.

The forming element 504 is provided with a number of through holes 530, 531. In the shown example, the holes go through both the liquid-permeable material layers 505', 505" and the absorbent structure 506 but it is possible, alternatively, to arrange holes only through the absorbent structure 506. The holes 530, 531 can have any suitable form and can also be in the form of channels. The number and size of the holes can also be varied. By selecting the location, size and mutual distance of the holes, it is possible to achieve different degrees of expansion inhibition in different parts of the absorbent structure. As a result, the absorbent structure has different stiffness in different areas after swelling. In this way, it is possible to obtain a forming element that has varying flexibility and therefore is formable or deformable to varying degrees in different areas. Generally, openings placed close together give greater stiffness in the area between the openings than openings spaced farther apart. It is therefore possible to create an absorbent article which adapts itself optimally to the body shape of the user due to the flexibility of the forming element.

Two oval holes 530 are arranged in the crotch portion 510 of the incontinence protector 500 and three circular holes 531 are arranged at each end portion 511 on the incontinence protector. When liquid meets the incontinence protector 500 and is absorbed by the absorbent structure 506, the absorbent structure swells in the thickness direction of the incontinence protector, as is shown in FIG. 6. The holes 530, 531 thus form liquid acquisition wells which can function as temporary reservoirs for liquid that has not yet been absorbed by the underlying absorption body 507. When the absorbent structure 506 expands, the space between the liquid-permeable material layers 505', 505" is filled until these layers limit further. expansion. The stiffness in the expanded material is thus increased so that the forming element 504, after expansion, also counteracts undesired, uncontrolled compression and deformation of the incontinence protector. The location of the oval holes 530 can mean that the holes can also serve as longitudinal bending indications for the incontinence protector 500, so that the parts between the holes 530 and the side edges 515, 516 are folded up when the incontinence protector 500 is compressed between the user's legs during use. The crotch portion 510 of the incontinence protector thus obtains a bowl shape adapted for liquid acquisition.

Therefore, it is possible to create a liquid-acquisition member which also serves as a forming member for an absorbent article during use.

The described embodiments shall not be considered to limit the invention but only constitute examples of applications of the invention. The expandable forming elements in the different embodiments can, of course, be used for other types of absorbent article than those described. It is, of course, also possible to combine the different forming elements with each other.

Example 1

Measurement of Expansion of Foam Material

When the expansion in the thickness direction of the material was measured, samples were punched out with a known diameter. The dry diameter ($d_t$) and the dry thickness ($t_t$) were measured. The samples were then allowed to swell for 1 minute in NaCl solution (0.9 weight percent NaCl). The wet diameter ($d_v$) and the wet thickness ($t_v$) were then measured.

The percentage thickness expansion (TE), the percentage area expansion (AE) and the percentage volume expansion (VE) were then calculated according to the formulae below.

$$TE=(t_v-t_t)/t_t \times 100$$

$$AE=(d_v^2-d_t^2)/d_t^2 \times 100$$

$$VE=(t_v d_v^2-t_t d_t^2)/t_t d_t^2 \times 100$$

The material which was tested is a polyacrylate-based foam which is denoted Foam XII. Foam XII has been manufactured according to the description below.

The following was added to a beaker:
348.5 grams acrylic acid (4.84 mol)
135.5 grams of a 37.3 weight percent natrium acrylate solution (0.54 mol)
28.0 grams polyethylene glycol diacrylate from polyethylene glycol with a mol mass of 400.
21.3 grams of a 15 weight percent water solution that contains ethylene oxide and linear C16C18 fat alcohol (mol ratio 80:1)
65.7 grams water This was mixed. The solution was then cooled to a temperature under 16 degrees Celsius. The solution was then poured into a sealed container, whereupon the solution was saturated with carbon dioxide gas at a pressure of 12 bar for 25 minutes. Under the same pressure, 26.7 grams of a water solution containing 3 weight percent of 2,2'-azobis(2-amidinopropane)dihydrochloride was added. This was mixed to form a homogenous solution. The solution was then allowed to rest for five minutes. The saturated solution was then pressed out of a container via a nozzle with an opening that was 1 mm at a pressure of 12 bar.

The resulting monomer foam was placed on a glass plate (DIN-A3). A further glass plate was then placed over the monomer foam. Thereafter, the foam was polymerised with a UV/VIS lamp, a UV1000 lamp from the Hönle company. The foam was illuminated with the lamp both from below and above. The illumination, and thus the polymerisation, was allowed to proceed for 4 minutes.

Results for Foam XII:

| $d_t$ | $t_t$ | $d_v$ | $t_v$ | TE | AE | VE |
|---|---|---|---|---|---|---|
| 28 | 3.8 | 62 | 6 | 58 | 357 | 622 |
| 28 | 3.8 | 61 | 6 | 58 | 390 | 577 |
| 28 | 3.8 | 62 | 6 | 58 | 390 | 649 |

The thickness expansion shall preferably be 40-80%, area expansion shall preferably be 300-400% and the volume expansion shall preferably be 500-800%.

Example 2

Absorption Capacity

The total absorption capacity per unit of volume of the absorbent structure in dry condition was determined for five different samples.

Sample A is a mixed structure of chemically-produced cellulose pulp from Weyerhauser and polyacrylate-based superabsorbent in particle form from BASF. The mixed structure contains 40 weight percent superabsorbent material, based on the total weight of the sample.

Sample B is a fibre structure from Weyerhauser. The fibre structure contains 80 weight percent cross-linked cellulose and 20 weight percent thermofibres.

Sample C is a polyester fibre layer with polyacrylate-based superabsorbent in particle form bound to the polyester fibre layer. Based on the total weight of the sample, the proportion of polyacrylate-based superabsorbent is 60 percent.

Sample D is a polyacrylate-based superabsorbent foam layer. The foam layer is denoted Foam XII and is described in detail in Example 1.

Sample E is a viscose foam, i.e. a foam of regenerated cellulose.

The measurement was carried out by first weighing the dry sample. The volume of the dry sample is then obtained by dividing the weight of the dry sample with the density of the dry sample. The sample was then saturated with a 0.9 weight percent NaCl-solution. The sample was provided with an excess of NaCl-solution and was allowed to absorb the liquid for 20 minutes. The saturated sample was then weighed. The amount of liquid which had been absorbed was obtained by subtracting the weight of the dry sample from the weight of the saturated sample.

The total absorption capacity, measured in grams of liquid per cubic centimeter of the absorbent material in dry condition was as follows:

| | Absorption capacity (grams liquid/cm$^3$) | | |
|---|---|---|---|
| Sample | $\rho = 0.50$ g/cm$^3$ | $\rho = 0.71$ g/cm$^3$ | $\rho = 0.91$ g/cm$^3$ |
| Sample A | 15 | 19 | 22 |
| Sample B | 6 | 6 | 8 |
| Sample C | 14 | 20 | 26 |
| Sample D | 27 | 38 | 49 |
| Sample E | 14 | 20 | 26 |

The result clearly shows that Foam XII, i.e. sample D, has a greater total absorption capacity, measured in grams of liquid per cubic centimeter of the absorbent material in dry condition.

Example 3

Stiffness of Sample Bodies with Limited Expansion Space

Figure 7:
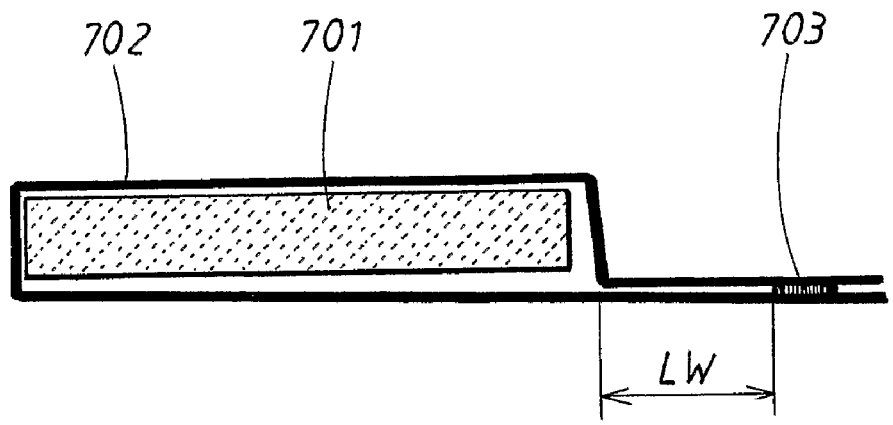
FIG. 7 shows a cross section through a test body for determination of swelling.

In order to investigate the change in the stiffness and thus the shape stability of the absorbent material which has been allowed to absorb liquid under conditions where the expansion ability of the absorbent material has been limited in accordance with the invention, the following test was carried out:

Sample bodies were produced from the various absorbent materials. The sample bodies were rectangular with a width of 0.01 m and a thickness of 0.0044 m. The length of the samples is not critical as long as it exceeds 0.04 m. The sample bodies were enclosed in a liquid-permeable tube-shaped nonwoven sleeve, as is shown in FIG. 7. The diameter of the sleeve 702 was chosen so that the sample 701 was left a certain pre-determined and limited expansion space defined by the length $L_w$ of the excess material which is shown in FIG. 7 between one of the ends of the sample and a weld 703 arranged to fasten the sleeve into a tube around the sample. As the thickness of the dry samples is negligible in these circumstances, the length $L_w$ gives a good measurement of the available expansion space.

12 samples were tested:

a) samples 1, 3, 5, 7, 9 and 11 consisted of a mixture of superabsorbent and chemical cellulose fluff pulp in the ratio 50/50 weight percent. The cellulose fluff pulp was southern pine NB 416 from Weyerhauser and the superabsorbent was BASF 7160. The nonwoven material used as a sleeve around the sample bodies was a polypropylene spunbond material with a basis weight of 16 g/m$^2$ from BBA Nonwovens, France.

b) samples 2, 4, 6, 8, 10, 12 consisted of Foam XII in accordance with Example 1 enclosed in a nonwoven sleeve of the same type as in a), i.e. a polypropylene spunbond material with a basis weight of 16 g/m$^2$ from BBA Nonwovens, France.

Test of Absorption Capacity and Volume of Enclosed Samples

I. Absorption Capacity:

The dry sample was weighed: $w_1$

Thickness and width of the dry sample were measured

The sample was put in a dish with 0.9% NaCl solution and was allowed to absorb for five minutes The sample was removed from the liquid and weighed: $w_2$ The sample was removed from the scale and the amount of liquid remaining on the scale was noted: $w_3$ The amount of NaCl solution which had been absorbed in grams per gram was calculated by subtracting the dry weight ($w_1$) of the sample and the weight of the liquid remaining on the scale ($w_3$) from the weight shown on the scale ($w_2$):

$$\text{Absorption (g/g)} = (w_2 - w_1 - w_3)/w_1$$

Two sample bodies were tested for each sample.

The test results are presented in Table 1 (superabsorbent/pulp mixture) and Table 2 (superabsorbent foam).

TABLE 1

| Sample | Dry weight $W_1$ | Dry width Sample + nw ($L_w$) (mm) | Weight after abs. $W_2$ | Weight remaining on scale $W_3$ | Absorbed Weight (g/g) | Wet volume (cm³) | Dry thickness (mm) |
|---|---|---|---|---|---|---|---|
| 1-1 | 1.08 | 10 + 0 | 10.55 | 0.21 | 8.6 | 10 | 4.3 |
| 1-2 | 1.05 | 10 + 0 | 10.21 | 0.22 | 8.5 | 9 | |
| 3-1 | 2.20 | 10 + 2 | 11.78 | 0.30 | 9.4 | 11 | 4.4 |
| 3-2 | 1.08 | 10 + 2 | 12.89 | 0.43 | 10.5 | 12 | |
| 5-1 | 1.14 | 10 + 4 | 14.77 | 0.54 | 11.5 | 14 | 4.2 |
| 5-2 | 1.11 | 10 + 4 | 14.31 | 0.15 | 11.8 | 14 | |
| 7-1 | 1.17 | 10 + 6 | 17.05 | 0.17 | 13.4 | 14 | 4.4 |
| 7-2 | 1.17 | 10 + 6 | 16.59 | 0.26 | 13.0 | 16 | |
| 9-1 | 1.18 | 10 + 8 | 18.02 | 0.45 | 13.9 | 17 | 4.25 |
| 9-2 | 1.19 | 10 + 8 | 18.66 | 0.29 | 14.4 | 18 | |
| 11-1 | 1.21 | 10 + 10 | 20.95 | 0.52 | 15.9 | 20 | 4.4 |
| 11-2 | 1.15 | 10 + 10 | 20.79 | 0.45 | 16.7 | 20 | |

TABLE 2

| Sample | Dry weight $W_1$ (g) | Dry width Prov + nw (Lw) (mm) | Weight after abs. $W_2$ (g) | Weight remaining on scale $W_3$ | Absorbed weight (g/g) | Wet volume (cm³) | Dry thickness (mm) |
|---|---|---|---|---|---|---|---|
| 2-1 | 0.78 | 10 + 0 | 7.69 | 0.60 | 8.1 | 7 | 3.4 |
| 2-2 | 0.76 | 10 + 0 | 6.91 | 0.18 | 7.9 | 7 | |
| 4-1 | 0.77 | 10 + 2 | 8.84 | 0.24 | 10.2 | 9 | 3.4 |
| 4-2 | 0.78 | 10 + 2 | 8.52 | 0.13 | 9.8 | 8 | |
| 6-1 | 0.81 | 10 + 4 | 10.99 | 0.10 | 12.4 | 11 | 3.4 |
| 6-2 | 0.78 | 10 + 4 | 12.48 | 0.32 | 14.6 | 12 | |
| 8-1 | 0.80 | 10 + 6 | 12.54 | 0.38 | 14.2 | 12 | 3.4 |
| 8-2 | 0.84 | 10 + 6 | 13.63 | 0.39 | 14.8 | 13 | |
| 10-1 | 0.82 | 10 + 8 | 16.55 | 0.50 | 18.6 | 16 | 3.4 |
| 10-2 | 0.82 | 10 + 8 | 14.89 | 0.34 | 16.7 | 15 | |
| 12-1 | 0.86 | 10 + 10 | 18.49 | 0.91 | 19.4 | 18 | 3.4 |
| 12-2 | 0.89 | 10 + 10 | 17.93 | 0.81 | 18.2 | 18 | |

II. Volume Increase

The sample was prepared by being wetted by an excess of NaCl solution for 5 minutes so that the sample absorbs liquid and expands.

A 100 ml measuring glass was filled with 70 ml 0.9% NaCl solution.

The liquid-saturated, swelled sample bodies were lowered into the measuring glass and the increase in volume was noted.

The method of measurement can be adapted according to the size of the sample. A larger or smaller measuring glass can be used, as can a different amount of liquid.

The volume increase in percent was calculated both based on the absorbed amount of liquid in grams/gram in accordance with method I, and based on the determination of displaced liquid in accordance with method II. As can be seen from Table 3 and Table 4, the methods give comparable results.

For the tested materials, complete expansion was reached when $L_w$ was 10 mm (10+10 in the tables) and essentially no expansion when $L_w$ was 0 mm.

TABLE 3

Calculation of expansion limitation

| Based on g/g-increase | Based on liquid displacement | Based on g/g-increase mean value | Based on liquid displacement mean value | Sample |
|---|---|---|---|---|
| 49% | 50% | 49% | 53% | 1 |
| 49% | 55% | | | |
| 43% | 45% | 40% | 43% | 3 |
| 37% | 40% | | | |
| 31% | 30% | 30% | 30% | 5 |
| 30% | 30% | | | |
| 20% | 30% | 21% | 25% | 7 |
| 22% | 20% | | | |
| 17% | 15% | 15% | 13% | 9 |
| 13% | 10% | | | |
| 5% | 0% | 2% | 0% | 11 |
| 0% | 0% | | | |

TABLE 4

Calculation of expansion limitation

| Based on g/g-increase | Based on liquid displacement | Based on g/g-increase mean value | Based on liquid displacement mean value | Sample |
|---|---|---|---|---|
| 58% | 61% | 59% | 61% | 2 |
| 60% | 61% | | | |
| 48% | 50% | 49% | 53% | 4 |
| 50% | 56% | | | |
| 36% | 39% | 30% | 36% | 6 |
| 25% | 33% | | | |
| 27% | 33% | 26% | 31% | 8 |
| 24% | 28% | | | |
| 4% | 11% | 9% | 14% | 10 |
| 14% | 17% | | | |
| 0% | 0% | 3% | 0% | 12 |
| 6% | 0% | | | |

Determination of Stiffness

The stiffness/shape stability for the swelled samples was measured by determining the elasticity module for the samples with an Instron 4301H1120, Software: Series IX.

The determinations of stiffness were carried out at 23° C. and 47% humidity.

Figure 8:
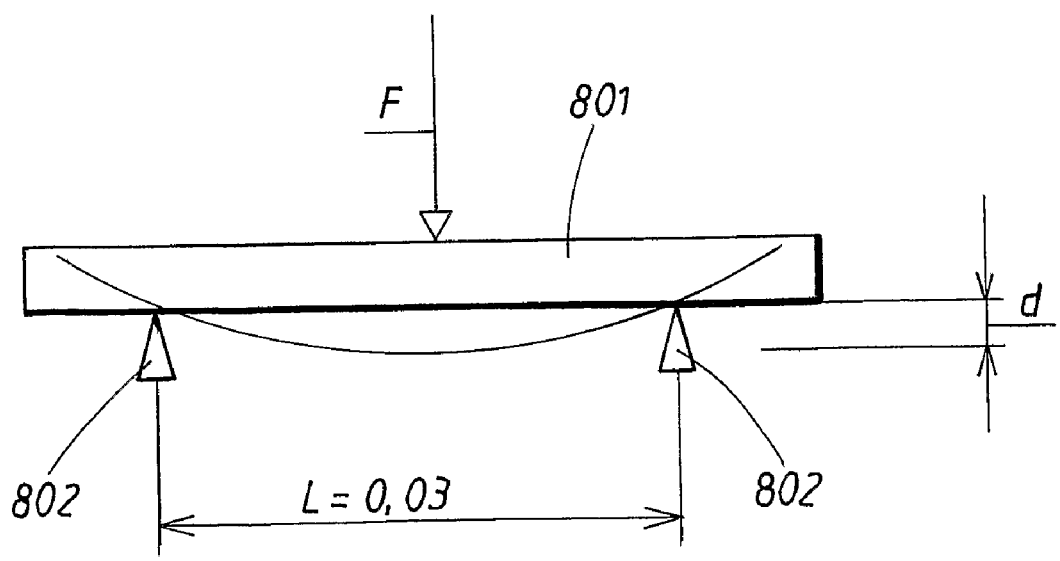
FIG. 8 shows a schematic picture of a test arrangement for measurement of stiffness.
Figure 9:
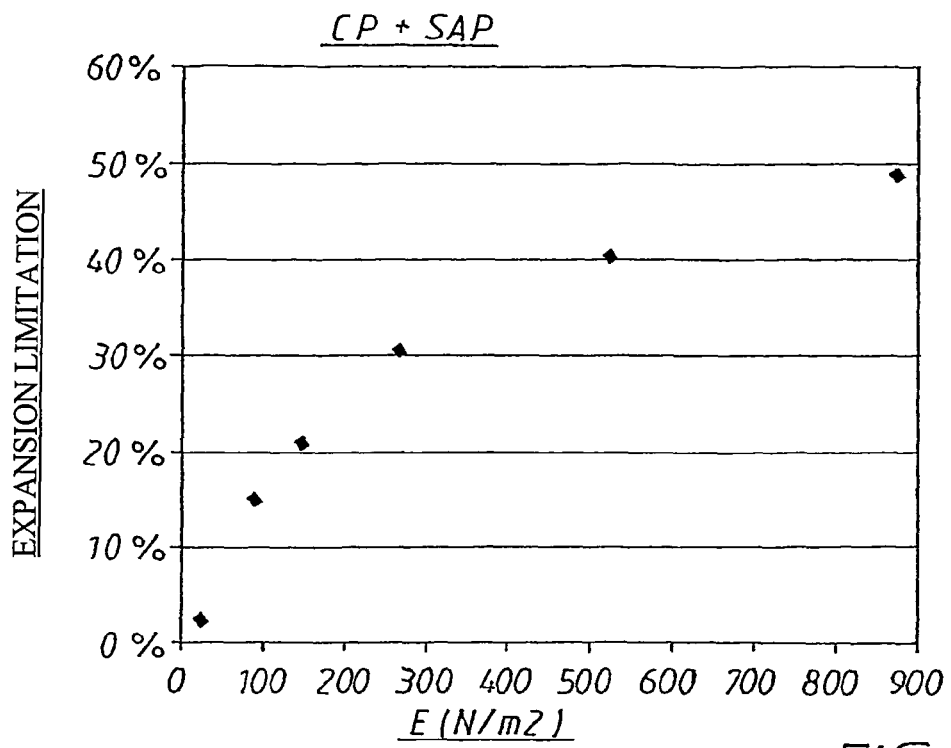
FIG. 9 shows Diagram 1.
Figure 10:
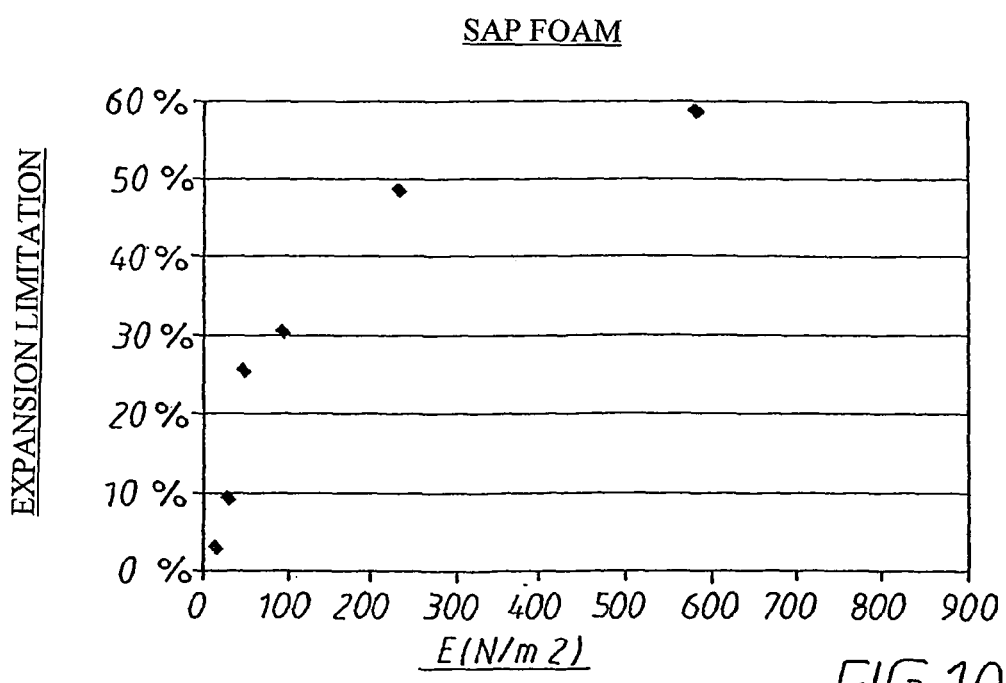
FIG. 10 shows Diagram 2

The test arrangement is shown schematically in FIG. 8. The swelled sample 801 was laid on two supports 802 placed at the distance L=0.03 m from each other. The test was carried out with a compression speed of 100 mm/min and the elasticity module E was calculated as a function of the compression force F and the curve d of the sample as follows:

$$E = F \times L^3 / d \times 48 \times I \, (N/m^2)$$

Where I is the moment of inertia and L is the distance between the supports 802.

Diagram 1 and Diagram 2 show the elasticity module E for the different samples as a function of the expansion limitation in percent. As can be seen in the diagrams, the elasticity module, and thus the stiffness of the sample, increases as the expansion space decreases.

Alternative Method for Estimating Expansion Inhibition; Test of Absorption Capacity for Enclosed and Opened Samples.

Weigh the dry, enclosed sample: $w_1$.

Lay the sample in a dish and add excess of 0.9% NaCl solution for five minutes.

Remove sample from liquid and weigh the wet sample: $w_2$

Remove sample from scale and note how much liquid remains on scale: $w_3$.

Calculate how much NaCl solution has been absorbed by the sample in grams per gram by subtracting dry weight ($w_1$) of sample and weight of remaining liquid ($w_3$) from weight shown by scale ($w_2$).

$$\text{Absorption (g/g)}: (w_2 - w_1 - w_3)/w_1$$

Weigh a polyester net, for example PE59HC from J.H. Tidbeck AB. This is a standard material which is used for different types of absorption tests, for example in the so-called Teabag Method. The net should have sufficient size to be able to retain the completely swelled sample in the liquid.

Cut open the sleeve/expansion-limiting material of the sample and place the sample on the polyester net.

Lay the polyester net with the sample in a dish with 0.9% NaCl solution and ensure that the sample has constant access to liquid. Let the sample absorb for five minutes.

Lift up the polyester net with the sample and weigh this: $W_4$.

Remove the sample from the scale by scraping the sample from the wet polyester net and note the weight of the polyester net and the liquid remaining on the scale: $w_5$.

Calculate how much NaCl solution the open sample has absorbed in grams per gram by subtracting the weight of the dry sample ($w_1$) and the polyester net and the remaining liquid ($w_5$) from the weight ($w_4$) of wet, completely expanded sample and divide this by the weight ($w_1$) of the dry sample.

$$\text{Absorption g/g} = (w_4 - w_1 - w_5)/w1.$$

The described method can be used, for example, to estimate the expansion limitation in a sample which has been taken from an absorbent article. If it is only of interest to measure the full expansion ability of the sample, the first, volume-limiting swelling step can be excluded. The sleeve of the dry sample is then cut open and placed directly onto a polyester net, whereafter the test is carried out with wetting and weighing as described above.

Samples Taken from Existing Absorbent Articles

For measurement of expansion limitation and stiffness in existing absorbent articles, measurements can be carried out either on whole expansion-limited elements in the article or on parts of such elements where samples can be taken out of the article without destroying the expansion-limiting means. For example, such a part element can be a piece of one of the raised, swellable liquid barriers 324, 325 in FIG. 3, or the delimited and enclosed part between the oval holes 530 in FIG. 5.

The invention is not limited to the embodiments described above and shown in the drawings, but may be varied within the scope of the claims, and equivalents thereof. In particular, the invention is not limited to a particular type of absorbent article, but the embodiments shown may be applied to any type of absorbent article. Details from the different embodiments may of course be combined as desired, as will be evident to the person skilled in the art.

The invention claimed is:

1. An absorbent article comprising a liquid-permeable surface layer and a liquid-impermeable surface layer and an absorption body arranged between the surface layers, the absorption body comprising a liquid-permeable material layer and an absorbent structure, the absorbent structure having the ability to expand on wetting and having a first volume in a dry condition and a second volume in a completely expanded wet condition, the second volume being greater than the first volume, wherein the liquid-permeable material layer constitutes a volume-limiting device for the absorbent structure so that the absorbent structure is prevented from reaching the completely expanded wet condition on wetting in an excess of 0.9% NaCl solution for 5 minutes and so that the absorbent structure after wetting in an excess of 0.9% NaCl solution for 5 minutes has a greater stiffness than in the dry condition and thus forms a forming element in the absorbent article, wherein the absorbent structure expands to a mean value of 70% or less of the completely expanded wet condition on wetting in an excess of 0.9% NaCl solution for 5 minutes, based on g/g increase.

2. The absorbent article in accordance with claim 1, wherein the absorbent structure can expand when wetted to a maximum volume which is ⅔ of the second volume of the absorbent structure.

3. The absorbent article in accordance with claim 1, wherein the absorbent structure comprises a polyacrylate-based foam material.

4. The absorbent article in accordance with claim 1, wherein the absorbent structure comprises a mixture of superabsorbent materials and fibres.

5. The absorbent article in accordance with claim 4, wherein the fibres comprise absorbent fibres.

6. The absorbent article in accordance with claim 5, wherein the absorbent fibres comprise cellulose fluff pulp.

7. The absorbent article in accordance with claim 1, wherein the liquid-permeable material layer comprises a nonwoven material.

8. The absorbent article in accordance with claim 1, wherein the liquid-permeable material layer comprises a perforated plastic film.

9. The absorbent article in accordance with claim 1, the absorbent article further comprising two longitudinal side edges, and the absorbent structure forms raised liquid barriers arranged along the longitudinal side edges.

10. The absorbent article in accordance with claim 1, wherein the absorbent structure in the dry condition has a density that is at least $0.5$ g/cm$^3$.

11. The absorbent article in accordance with claim 1, wherein the absorbent structure in the dry condition has a density that is at least $0.7$ g/cm$^3$.

12. The absorbent article in accordance with claim 1, wherein the total absorption capacity per cubic centimeter of the absorbent structure in the dry condition is at least 15 g/cm$^3$.

13. An absorbent article comprising a liquid-permeable surface layer and a liquid-impermeable surface layer and an absorption body arranged between the surface layers, the absorption body comprising a liquid-permeable material layer and an absorbent structure, the absorbent structure having the ability to expand on wetting and having a first volume in a dry condition and a second volume in a completely expanded wet condition, the second volume being greater than the first volume,
wherein the liquid-permeable material layer constitutes a volume-limiting device for the absorbent structure so that the absorbent structure is prevented from reaching the completely expanded wet condition on wetting in an excess of 0.9% NaCl solution for 5 minutes and so that the absorbent structure after wetting in an excess of 0.9% NaCl solution for 5 minutes has a greater stiffness than in the dry condition and thus forms a forming element in the absorbent article,
the absorbent article further comprising a thickness direction,
wherein the absorption body comprises an acquisition area for receiving body fluid, the acquisition area comprising at least a cavity or an area with a lower density than a part of the absorption body that is adjacent to the acquisition area and is situated chiefly in a single plane, and the part that is adjacent to the acquisition area comprises the absorbent structure, wherein the absorbent structure forms a raised barrier arranged on each side of the acquisition area in a longitudinal direction of the acquisition area, the absorbent structure chiefly increases in diameter in the thickness direction of the article during wetting and the size of the acquisition area increases in the thickness direction during wetting.

* * * * *